US006783002B1

(12) United States Patent
Pavlo

(10) Patent No.: US 6,783,002 B1
(45) Date of Patent: Aug. 31, 2004

(54) ANTI-NEEDLESTICK SYSTEM

(76) Inventor: John A. Pavlo, 1930 Temple Ter., Clearwater, FL (US) 33764

( * ) Notice: Subject to any disclaimer, the term of this patent is extended or adjusted under 35 U.S.C. 154(b) by 140 days.

(21) Appl. No.: 10/282,809

(22) Filed: Oct. 29, 2002

(51) Int. Cl.⁷ .............................................. B65D 83/10
(52) U.S. Cl. ...................................... 206/365; 206/470
(58) Field of Search ............................... 206/363, 364, 206/365, 366, 438, 467, 470; 604/110, 192

(56) References Cited

U.S. PATENT DOCUMENTS 5,133,454 A * 7/1992 Hammer ..................... 206/364
2002/0046962 A1 * 4/2002 Vallans et al.

* cited by examiner

Primary Examiner—Jacob K. Ackun, Jr.
(74) Attorney, Agent, or Firm—Edward P. Dutkiewicz

(57) ABSTRACT

An anti-needlestick system has a needle assembly with a needle in a 90 degree shaped configuration having flexible wings secured at an intermediate extent to the needle. A shield assembly is formed as a generally planar sheet with long side edges and short end edges and a slot at a central extent for receiving the wings of the needle assembly when held together and adapted to be placed beneath the wings above a patient's skin. The shield assembly is divided up into a male section on one side of the slot and a female section on the other side of the slot. Each section has an upwardly facing side wall along the side and end edges of the planar sheet. A locking member formed in the side wall includes a male locking member and a coacting female receptacle.

3 Claims, 3 Drawing Sheets

ANTI-NEEDLESTICK SYSTEM

BACKGROUND OF THE INVENTION

1. Field of the Invention

The present invention relates to an anti-needlestick system and more particularly pertains to precluding accidental piercing of a user's flesh when handling surgical needles.

2. Description of the Prior Art

The use of needle systems of known designs and configurations is known in the prior art. More specifically, needle systems of known designs and configurations previously devised and utilized for the purpose of safely handling surgical needles are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,772,638 to Utterberg, et al discloses a protector for needle. U.S. Pat. No. 5,330,438 to Gollobin et al. discloses a protective sheath for butterfly and IV infusion set and sheath assembly.

U.S. Pat. No. 5,219,339 to Saito discloses a single use medical needle. U.S. Pat. No. 5,176,655 to McCormick et al discloses a disposable medical needle and catheter placement assembly having full safety enclosure means. U.S. Pat. No. 5,069,341 to Barbieri, et al discloses a disposable single use drip feed device with a cover for the needle after use. U.S. Pat. No. 4,929,241 to Kulli discloses a medical needle puncture guard. U.S. Pat. No. 4,941,881 to Masters et al. discloses an IV infusion set with sheath. U.S. Pat. No. 4,676,783 to Jagger et al discloses a retractable safety needle. U.S. Pat. No. 4,160,450 to Doherty discloses an outside-the-needle catheter device with needle housing. U.S. Pat. No. 3,910,272 to Forberg discloses a flexible catheter. U.S. Pat. No. 3,670,727 to Reiterman discloses a medical infusion set. U.S. Pat. No. 3,610,249 to Harautuneian discloses an intravenous catheter apparatus with catheter telescoped inside puncturing cannula. U.S. Pat. No. 3,536,073 to Farb discloses a catheter placement apparatus. U.S. Pat. No. 3,572,334 to Peterson discloses an intravenous catheter placement unit. U.S. Pat. No. 3,055,361 to D. H. Ballard discloses intravenous catheters.

While these devices fulfill their respective, particular objectives and requirements, the aforementioned patents do not describe an anti-needlestick system that precludes accidental piercing of a user's flesh when handling surgical needles.

In this respect, the anti-needlestick system according to the present invention substantially departs from the conventional concepts and designs of the prior art, and in doing so provides an apparatus primarily developed for the purpose of precluding accidental piercing of a user's flesh when handling surgical needles.

Therefore, it can be appreciated that there exists a continuing need for a new and improved anti-needlestick system which can be used for precluding accidental piercing of a user's flesh when handling surgical needles. In this regard, the present invention substantially fulfills this need.

SUMMARY OF THE INVENTION

In view of the foregoing disadvantages inherent in the known types of needle systems of known designs and configurations now present in the prior art, the present invention provides an improved anti-needlestick system. As such, the general purpose of the present invention, which will be described subsequently in greater detail, is to provide a new and improved anti-needlestick system and method which has all the advantages of the prior art and none of the disadvantages.

To attain this, the present invention essentially comprises a needle assembly. The needle assembly has a needle in a 90 degree shaped configuration with a distal end formed with a point and a proximal end. A tube is coupled to the proximal end for introducing fluids to the needle and into a patient. The needle has flexible wings secured at an intermediate extent to the needle adjacent to the tube. The wings are adapted to lie in a flat orientation during operation and use. The wings are also adapted to be bent together in an essentially parallel relationship for being grasped by a health care giver when removing the needle from the patient. Next provided is a medication dispersing assembly. The medication dispersing assembly includes a generally frusto-conical implanted medication port with a hollow interior. The conical member has a plastic upper surface which is adapted to be pierced by the needle. The frusto-conical implanted medication port has an interior tube coupled to an appropriate portion of the patient's body to receive medication. The frusto-conical implanted medication port is adapted to be implanted beneath the skin of the patient. A shield assembly is next provided. The shield assembly is formed of a plastic material. The shield assembly is a generally planar sheet with long side edges and short end edges. A slot is provided at a central extent for receiving the wings of the needle assembly when held together and adapted to be placed beneath the wings above the patient's skin. The shield assembly is divided up into a male section on one side of the slot and a female section on the other side of the slot. Each section has an upwardly facing side wall along the side edges and end edges of the planar sheet. A locking member is next provided. The locking member includes a male locking member formed in the side wall adjacent the end edge of the male section. The locking member also includes a coacting female receptacle formed in the side wall adjacent the end edge of the female section for receiving the male locking member when the male and female sections are pressed together upon the removal of the needle from the patient. In this manner the needle is shielded from accidentally puncturing the skin of a health care giver. The side walls have male projections in the male section adjacent the slot and female receptacles in the female section adjacent the slot for guiding the proper orientation of the sections with respect to each other when secured for shielding a needle.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved anti-needlestick system which has all of the advantages of the prior art needle systems of known designs and configurations and none of the disadvantages.

Another object of the present invention is to provide an anti-needlestick system for precluding accidental piercing of a user's flesh when handling surgical needles.

It is another object of the present invention to provide a new and improved anti-needlestick system which may be easily and efficiently manufactured and marketed.

It is further an object of the present invention to provide a new and improved anti-needlestick system which is of reliable constructions.

An even further object of the present invention is to provide a new and improved anti-needlestick system which is susceptible of a low cost of manufacture with regard to both materials and labor, and which accordingly is then susceptible of low prices of sale to the consuming public, thereby making such anti-needlestick system economically available to the health care givers.

Lastly, it is an object of the present invention to provide a new and improved anti-needlestick system. A needle assembly has a needle in a 90 degree shaped configuration having flexible wings secured at an intermediate extent. A shield assembly is formed as a generally planar sheet with long side edges and short end edges and a slot at a central extent for receiving the wings of the needle assembly when held together and adapted to be placed beneath the wings above a patient's skin. The shield assembly is divided up into a male section on one side of the slot and a female section on the other side of the slot. Each section has an upwardly facing side wall along the side and end edges of the planar sheet. A locking member formed in the side wall includes a male locking member and a coacting female receptacle.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
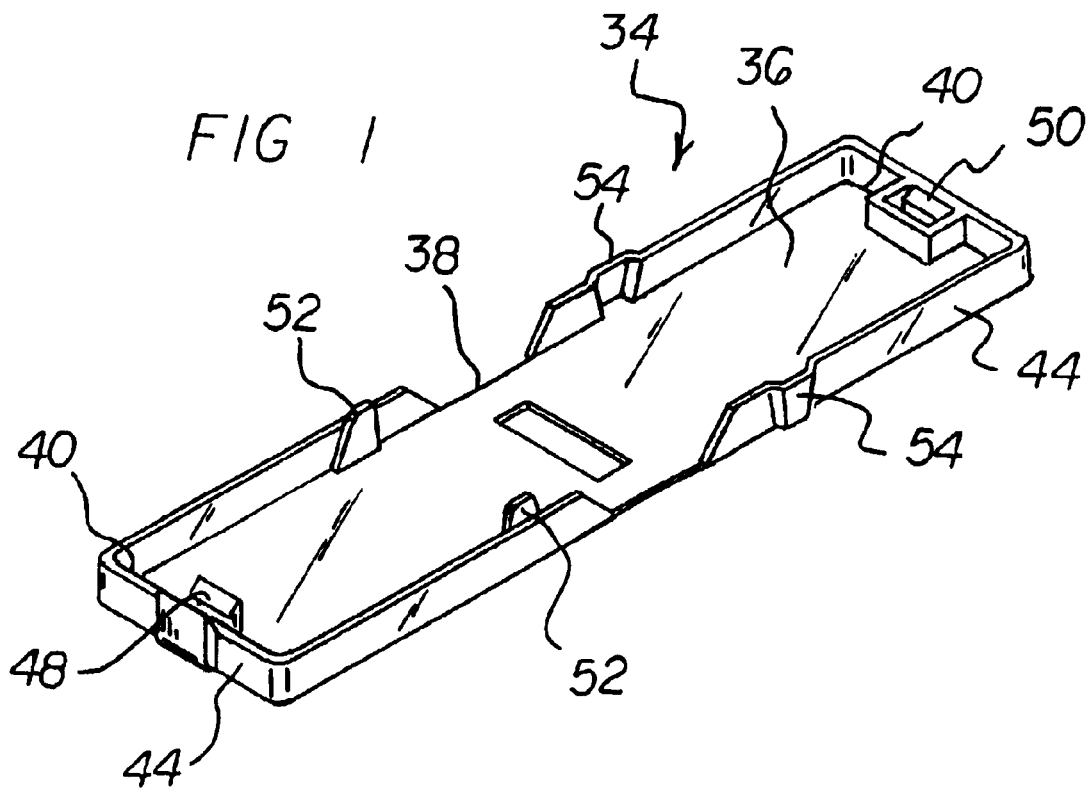
FIG. 1 is a perspective view of the shield assembly constructed in accordance with the principles of the present invention.
Figure 2:
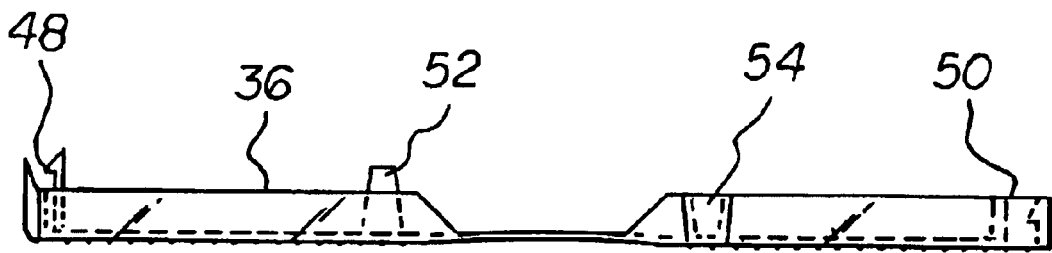
FIG. 2 is a side elevational view of the shielding assembly shown in FIG. 1.
Figure 3:
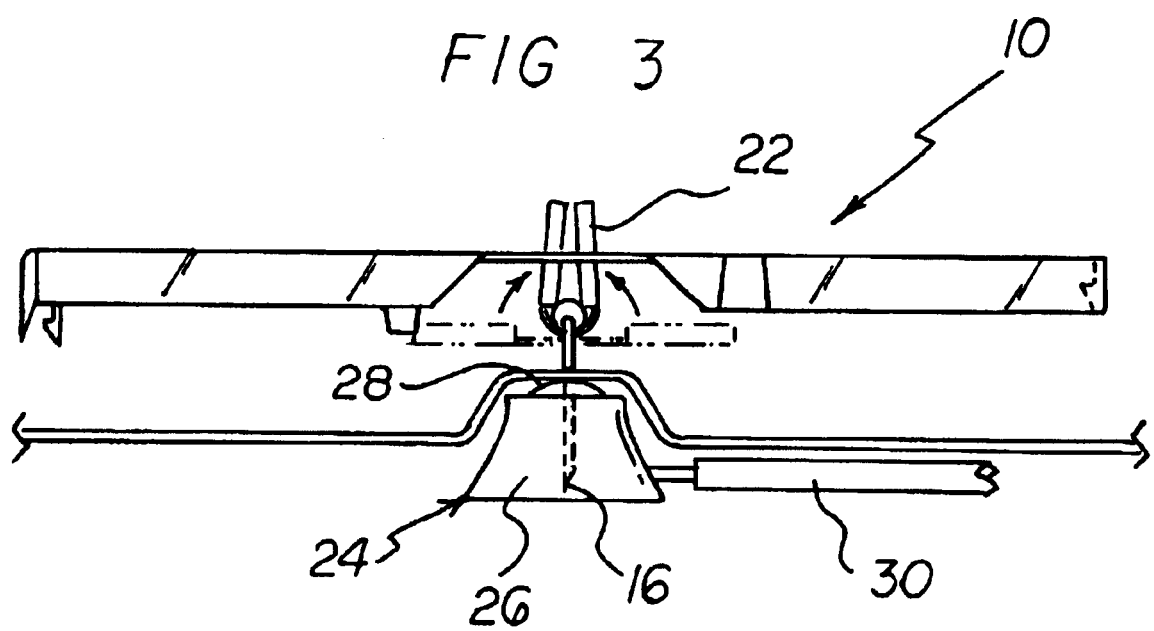
FIG. 3 is a side elevational view of the shielding assembly shown in FIG. 2 in orientation with respect to the other components of the system.
Figure 4:
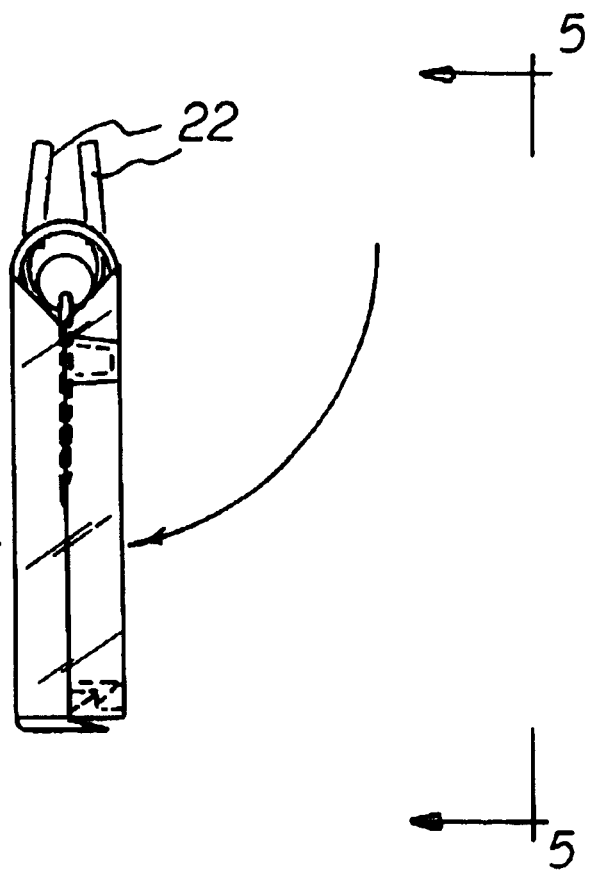
FIG. 4 is a side elevational view of the components shown in FIG. 3 but with the shield in a closed orientation.
Figure 5:
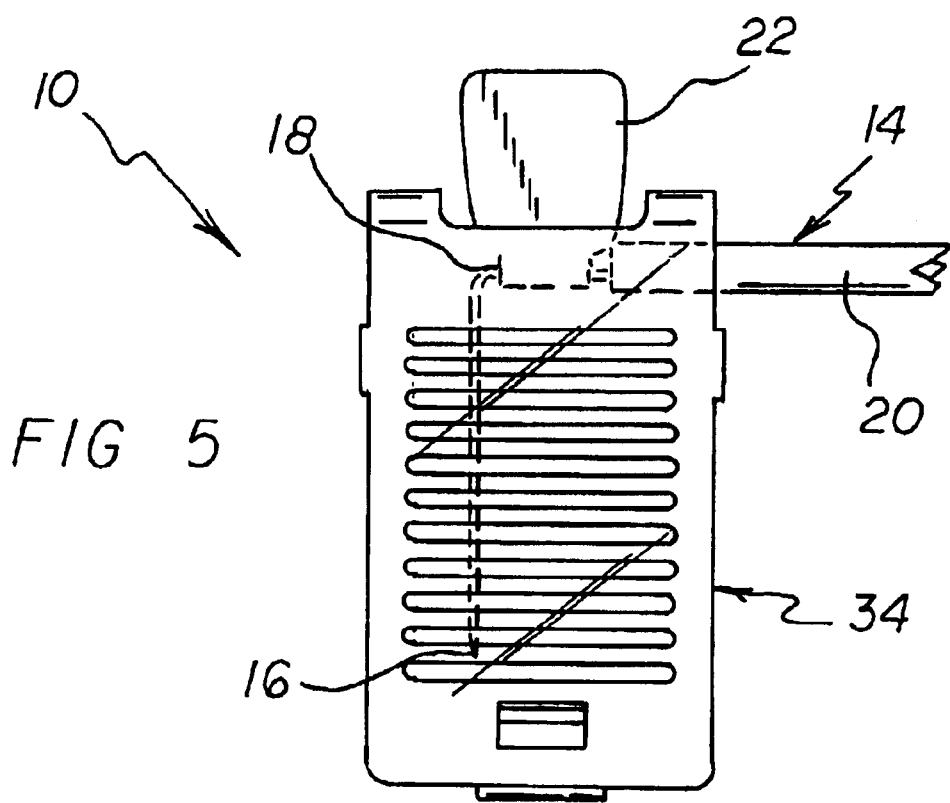
FIG. 5 is a side elevational view taken along line 5—5 of FIG. 4.
Figure 6:
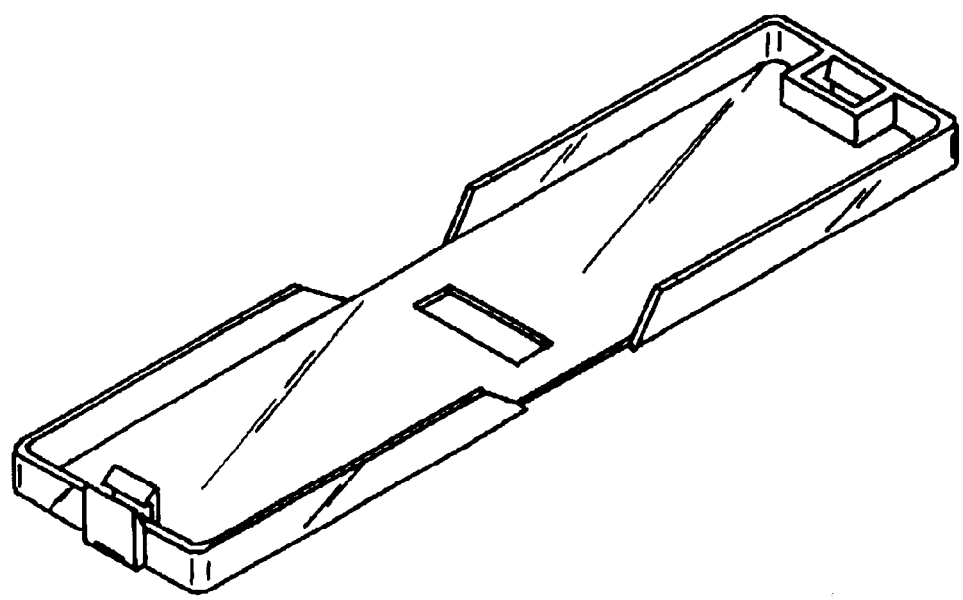
FIG. 6 is a perspective view of an alternate embodiment of the invention without the alignment mechanisms.

With reference now to the drawings, and in particular to FIG. 1 thereof, the preferred embodiment of the new and improved anti-needlestick system embodying the principles and concepts of the present invention will be described.

The present invention, the anti-needlestick system 10 is comprised of a plurality of components. Such components in their broadest context include a needle assembly and a shield assembly. Such components are individually configured and correlated with respect to each other so as to attain the desired objective.

First provided is a needle assembly 14. The needle assembly has a needle in a 90 degree shaped configuration with a distal end 16 formed with a point and a proximal end 18. A tube 20 is coupled to the proximal end for introducing fluids to the needle and into a patient. The needle has flexible wings 22 secured at an intermediate extent to the needle adjacent to the tube. The wings are adapted to lie in a flat orientation during operation and use. The wings are also adapted to be bent together in an essentially parallel relationship for being grasped by a health care giver when removing the needle from the patient.

Next provided is a medication dispersing assembly 24. The medication dispersing assembly includes a generally frusto-conical implanted medication port 26 with a hollow interior. The conical member has a plastic upper surface 28 which is adapted to be pierced by the needle. The frusto-conical implanted medication port has an interior tube 30 coupled to an appropriate portion of the patient's body to receive medication. The frusto-conical implanted medication port is adapted to be implanted beneath the skin of the patient.

A shield assembly 34 is next provided. The shield assembly is formed of a plastic material. The shield assembly is a generally planar sheet 36 with long side edges 38 and short end edges 40. A slot 42 is provided at a central extent for receiving the wings of the needle assembly when held together and adapted to be placed beneath the wings above the patient's skin. The shield assembly is divided up into a male section on one side of the slot and a female section on the other side of the slot. Each section has an upwardly facing side wall 44 along the side edges and end edges of the planar sheet.

Next provided as part of the shield assembly is a locking member. The locking member includes a male locking member 48 and a coacting female locking receptacle 50. The male locking member is formed in the side wall adjacent the end edge of the male section. The coacting female receptacle 50 is formed in the side wall adjacent the end edge of the female section. The female locking member receives the male locking member when the male and female sections are pressed together upon the removal of the needle from the patient. In this manner the needle is shielded from accidentally puncturing the skin of a health care giver. The side walls have male projections 52 in the male section adjacent the slot and female receptacles in the female section 54 adjacent the slot for guiding the proper orientation of the sections with respect to each other when secured for shielding a needle. Needles have various lengths, normally from ½ inch to 1½ inches. The present invention is designed to cover essentially all needle lengths.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An anti-needlestick system for precluding accidental piercing of a user's flesh when handling surgical needle comprising, in combination:
    a needle assembly having a needle in a 90 degree shaped configuration with a distal end formed with a point and a proximal end, a tube coupled to the proximal end for introducing fluids to the needle and into a patient, the needle having flexible wings secured at an intermediate extent to the needle adjacent to the tube, the wings adapted to lie in a flat orientation during operation and use but adapted to be bent together in an essentially parallel relationship for being grasped by a health care giver when removing the needle from the patient;
    a medication dispersing assembly including a generally frusto-conical implanted medication port with a hollow interior and a plastic upper surface adapted to be pierced by the needle, the frusto-conical implanted medication port having an interior tube coupled to an appropriate portion of the patient's body to receive medication, the frusto-conical implanted medication port adapted to be implanted beneath the skin of the patient;
    a shield assembly formed of a plastic material with a generally planar sheet with long side edges and short end edges and with a slot at a central extent for receiving the wings of the needle assembly when held together and adapted to be placed beneath the wings above the patient's skin, the shield assembly being divided up into a male section on one side of the slot and a female section of the other side of the slot, each side having an upwardly facing side wall along the side edges and end edges of the planar sheet, a locking member including a male locking member formed in the side wall adjacent the end edge of the male section and a coacting female receptacle formed in the side wall adjacent the end edge of the female section for receiving the male locking member when the male and female sections are pressed together upon the removal of the needle from the patient to thereby shield the needle from accidental puncturing of the flesh of a health care giver, the side walls having male projections in the male section adjacent the slot and female receptacles in the female section adjacent to the slot for guiding the proper orientation of the sections with respect to each other when secured for shielding a needle.

2. An anti-needlestick system comprising:
    a needle assembly having a needle in a 90 degree shaped configuration having flexible wings secured at an intermediate extent to the needle;
    a shield assembly with a generally planar sheet with long side edges and short end edges and with a slot at a central extent for receiving the wings of the needle assembly when held together and adapted to be placed beneath the wings above a patient's skin, the shield assembly being divided up into a male section on one side of the slot and a female section on the other side of the slot, each section having an upwardly facing side wall along the side and end edges of the planar sheet, and having a locking member including a male locking member and a coacting female receptacle formed in the upwardly facing side wall.

3. The system as set forth in claim 2 wherein the shield assembly is formed of a plastic material.

* * * * *